United States Patent [19]

Kozin et al.

[11] Patent Number: 4,771,784

[45] Date of Patent: Sep. 20, 1988

[54] OPHTHALMORHEOGRAPHIC TRANSDUCER

[75] Inventors: Mikhail P. Kozin; Nikolai V. Kudashov; Jury I. Sakharov, all of Kuibyshev; Svyatoslav N. Fedorov, Moscow, all of U.S.S.R.

[73] Assignees: Kuibyshevksy Politekhnichesky Institut, Kuibyshev; Moskovsky Nii Mikrohirurgii Glaza, Moscow, both of U.S.S.R.

[21] Appl. No.: 15,620

[22] Filed: Feb. 17, 1987

[51] Int. Cl.4 .............................................. A61B 5/04
[52] U.S. Cl. .................................................... 128/643
[58] Field of Search ............................... 128/643, 802

[56] References Cited

U.S. PATENT DOCUMENTS 3,367,323 2/1968 Schuler ........................... 128/643 X
3,505,993 4/1970 Lewes et al. ...................... 128/643

FOREIGN PATENT DOCUMENTS 1024061 6/1983 U.S.S.R. ............................. 128/643

OTHER PUBLICATIONS

Intraocular Pressure/Physiology and Pathology, by A. Nesterov, A. Bunin and L. Katsnelson (MIR Publishers-Moscow), 1974.

Primary Examiner—Lee S. Cohen
Attorney, Agent, or Firm—Lilling & Greenspan

[57] ABSTRACT

An ophthalmorheographic transducer has a two-layer casing with a space defined between the layers and communicating with a vacuum source. The inner layer is shaped so as to suit the eyeball, is provided with electrodes and has a plurality of openings.

1 Claim, 1 Drawing Sheet

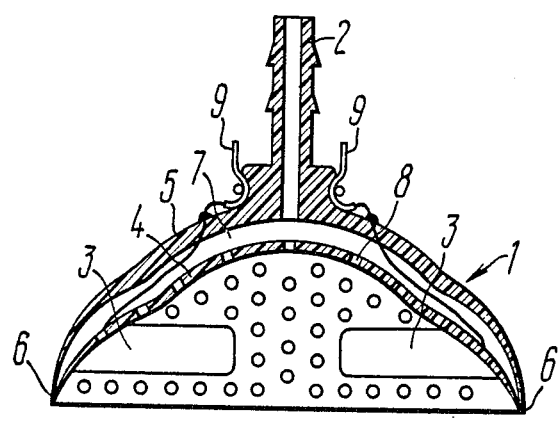

OPHTHALMORHEOGRAPHIC TRANSDUCER

BACKGROUND OF THE INVENTION

1. Field of Application

The invention relates to medical instruments to to be used in the field of ophthalmology, and more specifically, it deals with an ophthalmorheographic transducer for examination of the eye hemodynamics.

2. Description of the Prior Art

Recording variations of the impedance of the eye tissues is an important technique in the examination of blood circulation in the eye. The design of an ophthalmorheographic transducer used for this purpose is vitally important.

Known in the art is a Bettelheim ophthalmorheorgaphic transducer having a casing which is made of an insulating material and has a spheric inner surface for engaging the surface of the eyeball, electrodes on the inner surface of the casing, and a pipe for connecting the casing to a vacuum source (cf. A. P. Nesterov et al. Intraocular Pressure (Physiology and Pathology). Moscow., Nauka Publishing House, 1974, pp. 194–207). When this transducer is used, contact between the eyeball surface and electrodes and retention of the transducer casing on the eye are accomplished by providing vacuum between the inner surface of the casing and the surface of the eyeball. However, because of compression of the eye caused by vacuum application, hemodynamics of the eye is disturbed, and the resultant rheographic recording cannot be considered as reliable. In addition, it is difficult to ensure uniform pressure of the electrodes. Practice has shown that it is only the central portion of the transducer casing that is intimately pressed and retained, the intimacy of contact along the edges being affected so that impedance is mainly a function of the contact surface area rather than a function of changes in blood filling.

SUMMARY OF THE INVENTION

It is the main object of the invention to improve accuracy of measurement of changes in the impedance of the eye tissues.

Another object of the invention is to ensure uniformity of pressure of the electrodes against the surface of the eyeball.

Still another object of the invention is to eliminate any influence of the degree of pressure reduction during vacuum application on intraocular pressure and nemodynamics of the eye.

The invention consists of ophthalmorheographic transducer comprising a casing of an electrically insulating material having a spherical inner surface, which is adapted to be in contact with the surface of the eyeball, electrodes on the inner surface of the casing, and a pipe for connecting the casing to a vacuum source. According the invention, the casing is made up of two layers which are sealingly interconnected along the perimeter of the casing so as to define a space between the layers communicating with the pipe, the inner layer being shaped so as to suit the eyeball and being made with a plurality of through openings.

The ophthalmorheographic transducer according to the invention ensures uniform intimacy of contact between the electrodes and the eyeball surface during measurements so as to eliminate any influence of the degree of pressure reduction during vacuum application on intraocular pressure thus making it possible to carry out objective examinations of the eye hemodynamics and contributing to an exact diagnosis. The transducer is simple in manufacture and reliable in operation.

BRIEF DESCRIPTION OF THE DRAWING

The invention will now be described with reference to a specific embodiment thereof and the accompanying drawing which shows a general view of an ophthalmorheographic transducer according to the invention, in cross-section.

DESCRIPTION OF THE PREFERRED EMBODIMENT

An ophthalmorheographic transducer according to the invention is in the form of a two-layer spherical casing 1 made of an electrically insulating material, having a pipe 2 for connecting to a vacuum source (not shown in the drawing), and electrodes 3 disposed on the inner surface thereof. An inner layer 4 and an outer layer 5 of the casing 1 are sealingly interconnected along the perimeter of the casing 1 at 6, and a space 7 is defined between the layers 4 and 5, which communicates with the pipe 2. The inner layer 4 is shaped so as to suit the eyeball and is made with a plurality of through openings 8. Leads of the electrodes 3 sealingly extend outside the casing 1 and are connected to external conductors 9 to be connected to a rheorgraph (not shown in the drawing).

The ophthalmorheographic transducer functions in the following manner.

The casing 1 is positioned on the eye in such a manner that the eye cornea should be located at the center of the casing 1. Vacuum is created in the space 7 and between the layer 4 and the surface of the eyeball by means of a vacuum source through the pipe 2 and the openings 8. The inner surface of the layer 4 will thus be tightly pressed against the eye surface so as to ensure an intimate and uniform contact of the eye tissues with the whole surface of the electrodes 3. The rigidity of the inner layer 4 chosen is such that the layer is not deformed under the action of vacuum and any deformation of the anterior part of the eye is precluded, which fact is extremely important in conducting hemodynamic examinations. The layer 4 may be made, e.g. of polymethylmethacrylate. The provision of the inner layer 4 which is shaped to suit the eyeball and which has openings 8 makes it possible to prevent misplacement of the casing 1 on the eye.

We claim:

1. An ophthalmorheographic transducer comprising:
   a casing of an electrically insulating material, which is made up of two layers one of which is an outer layer and the other of which is an inner layer, said inner layer having one surface thereof adapted to be in contact with the surface of the eyeball, said two layers being sealingly interconnected along a perimeter of said casing and a space being defined between said outer and inner layers;
   a pipe communicating with said space, adapted to be connected to a vacuum source, said inner layer being generally rigid and shaped so as to conform to the shape of the eyeball to be examined;
   a plurality of through openings made in said inner layer; and
   electrodes provided on an inner surface of said inner layer which is adapted to be in contact with the surface of the eyeball;

whereby said inner surface of said inner layer can be tightly pressed against the surface of the eyeball to ensure intimate and uniform contact between the tissues of the eyeball and said electrodes without deformation of the eyeball due to the action of the vacuum applied to said space, and, through said openings, to the surface of the eyeball.

* * * * *

UNITED STATES PATENT AND TRADEMARK OFFICE
CERTIFICATE OF CORRECTION

PATENT NO. : 4,771,784

DATED : September 20, 1988

INVENTOR(S) : Mikhail P. Kozin, et al.

It is certified that error appears in the above-identified patent and that said Letters Patent is hereby corrected as shown below:

On the Title Page, add --[30] Foreign Applications Priority Data

February 25, 1986 [SU] U.S.S.R. 4023143

Signed and Sealed this

Eleventh Day of July, 1989

Attest:

DONALD J. QUIGG

Attesting Officer

Commissioner of Patents and Trademarks